US00PP13660P29

(12) United States Plant Patent
Zerr

(10) Patent No.: US PP13,660 P2
(45) Date of Patent: Mar. 18, 2003

(54) POINSETTIA PLANT NAMED 'FISMILLE'

(75) Inventor: Katharina Zerr, Simmern (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/210,123

(22) Filed: Dec. 11, 1998

(51) Int. Cl.[7] ..... A01H 5/00

(52) U.S. Cl. ..... Plt./307

(58) Field of Search ..... Plt./307

(56) References Cited

U.S. PATENT DOCUMENTS 4,724,276 A * 2/1988 Ecke, Jr. ..... 47/58
PP9,336 P * 10/1995 Beckmann ..... Plt./306

OTHER PUBLICATIONS

UPOV–ROM GTITM Computer Databse 1999/02, GTI JOUVE Retrieval Software, citations for 'Fismille', May 1999.*
German Application–FISMILLE–Dec. 15, 1997.
German Denomination–FISMILLE–Aug. 15, 1998.
Canadian Application–FISMILLE–Aug. 18, 1997.
Fischer Poinsettia Catalogue–Germany (1998), p. 16 (FISMILLE).

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

'Fismille' is characterized by bright red bract color; relatively large, slightly reflexed involucre formed by ovate and somewhat folded bracts; dark-green foliage which is narrow and ovately shaped with only very weak lobes; very early flowering response; and vigorous growth, in combination with medium to tall, upright plant habit.

1 Drawing Sheet

BACKGROUND OF THE INVENTION

The present invention relates to a new and distinct cultivar of Poinsettia plant known by the cultivar name 'Fismille' and botanically known as *Euphorbia pulcherrima*.

'Fismille' is a product of a planned breeding program which had the objective of creating new poinsettia cultivars with red bract color, dark-green foliage, good branching characteristics and early flowering response. 'Fismille' was originated from a hybridization made in a controlled breeding program in Hillscheid, Germany, in 1993.

The female parent was a proprietary, hybrid seedling, No. S90-502-1, characterized by red bract color, dark-green foliage and early flowering. The male parent was a hybrid seedling, no. S90-202-1, with light-red bracts and medium-green foliage. 'Fismille' was discovered and selected as one flowering plant (no. 2299) within the progeny of the stated parentage by Katharina Zerr in the autumn of 1994 in a controlled environment in Hillscheid, Germany.

The seeds from the hybridization made in February 1994, and the seedlings therefrom, were identified by numbers. In the summer of 1994, a cutting was taken from each seedling and grown as a flowering, single-stem plant for examination and selection in the autumn. After plant no. 2299 had been chosen, more cuttings were taken from the original seedling and grafted on rootstocks of variety 'Beckmanns Altrosa' (U.S. Plant Pat. No. 9,336) in order to transmit the phytoplasma suspected of causing branching. The cuttings used were new shoot tips (short stem with 3–4 mature leaves) from the upper area of the plant taken from branches emerging from the main stem higher than the place of grafting. From cuttings of these grafted plants, branched plants were grown for the trial cultivation (horticutural examination) in autumn and winter of 1995 to 1996. Horticultural examination initiated in autumn of 1995 and continuing thereafter has demonstrated that the combination of characteristics as herein disclosed for 'Fismille' are firmly fixed and are retained through successive generations of asexual reproduction.

BRIEF DESCRIPTION OF THE INVENTION

The following traits have been repeatedly observed and are determined to be basic characteristics of 'Fismille' which in combination distinguish this Poinsettia as a new and distinct cultivar:

1. Bright red bract color;

2. Relatively large, slightly reflexed involucre formed by ovate and somewhat folded bracts;

3. Dark-green foliage, narrow ovately shaped and with only very weak lobes;

4. Very early flowering response; and

5. Vigorous growth, in combination with medium to tall, upright plant habit.

'Fismille' has not been observed under all possible environmental conditions. The phenotype may vary significantly with variations in environment such as temperature, light intensity, and daylength without a change in genotype. The following observations, measurements and comparisons describe plants grown in Langley, British Columbia, Canada, under greenhouse conditions which approximate those generally used in commercial practice.

Of the many commercial varieties known to the inventor, the most similar in comparison to 'Fismille' is the patented cultivar 'Freedom Red' (U.S. Plant Pat. No. 7,825). In comparison to 'Freedom Red', 'Fismille' has more intense and brighter red-colored bracts, which do not tend to fade at high temperature. Bracts and leaves of 'Fismille' develop hardly any lobes in contrast to 'Freedom Red' which is moderately lobed. Furthermore, the plant habit of 'Fismille' is usually somewhat taller, but narrower, than 'Freedom Red' and flowering begins even earlier.

BRIEF DESCRIPTION OF THE DRAWING

The accompanying color photographic sheet shows typical inflorescence and foliage of a mature potted plant of 'Fismille', with colors being as true as possible with illustrations of this type.

DETAILED BOTANICAL DESCRIPTION

The plants described herein were grown in a greenhouse in Langley, British Columbia, Canada, in autumn of 1997. Rooted cuttings were planted into 15-cm pots on August 1, and were pinched on August 18, leaving 8 nodes. The minimum temperature was 23° C. until October 10, 20° C. to mid-November, and lower thereafter. The plants initiated flowers under natural short-day conditions in autumn.

The cultivars 'Fisnova', 'Fismille' and 'Fisgala' are compared in the following chart:

| | FISNOVA | FISMILLE | FISGALA |
|---|---|---|---|
| Bract color | medium to dark red | Brilliant, medium red | Dark red, often more bluish than: |
| Upper Surface RHS | 46 B | 45 A | 46 B |
| Lower surface RHS | 46 B-C | 46 B | 46 B |
| Stem color | Light to medium green, | Medium green, | Medium green, |
| Infusion of anthocyanin | 137 C weak | 137 B weak | 137 B strong |
| Foliage, lobes | weak | almost no lobes | weak to medium |
| Growth/ Plant habit | Medium vigor, rel. compact as a young plant, develops later a more round plant habit when given enough space so that all the branches may develop fairly evenly * | vigorous, medium to tall, upright plant habit | moderately vigorous growth, medium height, V-shaped plant habit with uniformly developed brances |
| No. of branches | 8.5 | 6.9 | 7.5 |
| Begin of flowering | 8.5 weeks | 7.5 weeks | 8–8.5 weeks |

In the following description, color references are made to The Royal Horticultural Society Colour Chart (R.H.S.). The color values were determined indoors in a north light.

Classification:

*Botanical.*—*Euphorbia pulcherrima.*

*Commercial.*—Poinsettia, cv. 'Fismille'.

Parentage:

*Female parent.*—Hybrid seedling no. S90-502-1.

*Male parent.*—Hybrid seedling no. S90-202-1.

Plant:

*Form.*—Shrub, self-branching.

*Growth habit.*—Vigorous growth, plant habit of branched plants is medium to tall, but not very wide, with branches directed upwardly. Height, including pot, is 48.5 cm. The average number of branches is 6.9.

*Rooting.*—Fast, less than 20 days.

*Stem color.*—Medium-green, R.H.S. 137 B, with only weak infusion of anthocyanin.

*Blooming habit.*—Flowering response time under natural short-day conditions in autumn: botanically, cyathia open, around November 24; commercially, bracts colored and marketable, in mid-November.

*Flowering response time.*—About 7.5 weeks.

*Keeping quality of bracts and leaves ('shelf life').*—Good, typically for the dark-leafed varieties, on the condition that plants have not been grown under overhead irrigation.

Foliage:

*Shape.*—Narrow ovate with slightly rounded almost straight base, acuminated tip, and almost no lobes.

*Margin.*—Entire.

*Texture.*—Upper surface: Smooth and flat, only weakly veined, veins hardly visible, R.H.S. 146 D, basal part of midrib may have the same reddish coloring as the petiole. Lower surface: Flat and smooth, except for the slightly protruding midrib and finer side veins, which are arranged in a herringbone pattern; the vein color is a light green, R.H.S. 139 D, or lighter than R.H.S. 180 D, when primarily younger leaves are partly infused with anthocyanin.

*Size.*—Leaf blade length is 13.5 cm, leaf blade width is 8.8 cm; petiole length is 7.5 cm.

*Color.*—Generally a uniform dark-green. Mature foliage: Upper surface is R.H.S. 139 A; under surface is R.H.S. 137 B. New foliage: Upper side is about R.H.S. 143 B; under side is about R.H.S. 143 C.

*Petiole color.*—Red to dark-red, near R.H.S. 53A.

*Aspect.*—Petioles and leaves are horizontally directed.

*Disease resistance.*—Typical, no special observations made.

Flowering description:

*Inflorescence.*—Relatively large, with the bracts slightly upwards directed, and reflexed, well-closed center. The diameter of inflorescence is 29.5 cm.

*Number of inflorescence per plant.*—5.5–6.0.

*Number of bracts per inflorescences.*—9–10 true bracts, length over 3 cm.

*Size of bract.*—The length of the largest fully colored bract is 14.2 cm and the width is 10.4 cm; petiole is 2.5 cm.

*Bracts, shape.*—Ovate-shaped, with slightly rounded base, acuminated tip, and usually no lobes.

*Texture.*—Distinctly rugose, and folded along the midrib, the veins are arranged in a 'herringbone' pattern and are hardly visible on the upper surface; the vein color of the upper side corresponds to the bract color or appears slightly darker, while on the lower surface, the veins are usually lighter, pink to rose-red R.H.S. 51 A to 52 A, or lighter.

*Color.*—Generally an intense bright-red, uniform, and without tendency to fading near the margin, nor under high temperature conditions. Upper surface: Near R.H.S. 45 A. Lower surface: R.H.S. 46 B.

*Petiole, color.*—(Dark) red, R.H.S. 46 A–B.

*Cyathia.*—Few, about 10 in a narrow cluster, about 25 mm wide; diameter of the single cyathium is 6 mm.

*Color.*—Mainly light-green, R.H.S. 143 B or lighter; top is red, about R.H.S. 46 B.

*Retention.*—Average, better than 'Freedom Red'.

*Nectar cups.*—Small to medium-sized, golden yellow, margin usually without anthocyanin coloring.

Reproductive organs:

*Stamens.*—Red filaments, fertile, yellow pollen.

*Pistils.*—Style and stigma are red, 6-lobed stigma.

*Ovaries.*—Triangular, 3 ovules.

*Seed set/fruit.*—Few seeds are formed spontaneously, they are but fertile when pollinated.

*Shape and development.*—Typical for the specifics.

I claim:

1. A new and distinct poinsettia plant named 'Fismille', substantially as illustrated and described.

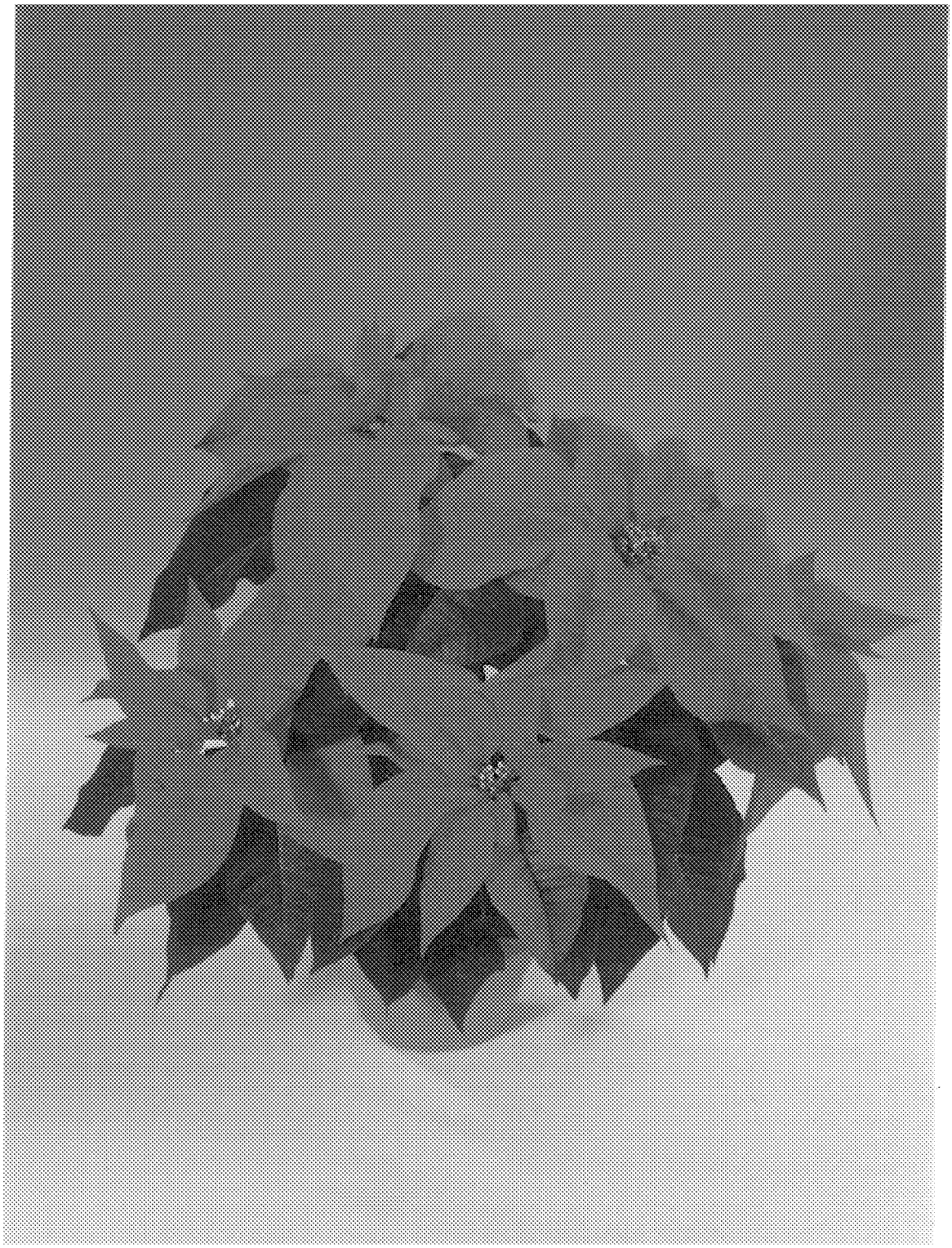

* * * * *